United States Patent
Abele et al.

(10) Patent No.: US 9,834,801 B2
(45) Date of Patent: Dec. 5, 2017

(54) METHODS FOR THE SYNTHESIS OF CHIRAL KYNURENINE COMPOUNDS

(71) Applicant: VISTAGEN THERAPEUTICS, INC., South San Francisco, CA (US)

(72) Inventors: Stefan Abele, Oberwil (CH); Klaus Laue, Buchs (CH); Roland A. Breitenmoser, Obermumpf (CH)

(73) Assignee: VISTAGEN THERAPEUTICS, INC., South San Francisco, CA (US)

(*) Notice: Subject to any disclaimer, the term of this patent is extended or adjusted under 35 U.S.C. 154(b) by 0 days.

(21) Appl. No.: 14/775,287

(22) PCT Filed: Mar. 14, 2014

(86) PCT No.: PCT/US2014/027694
§ 371 (c)(1),
(2) Date: Sep. 11, 2015

(87) PCT Pub. No.: WO2014/152752
PCT Pub. Date: Sep. 25, 2014

(65) Prior Publication Data
US 2016/0032334 A1 Feb. 4, 2016

Related U.S. Application Data

(60) Provisional application No. 61/785,807, filed on Mar. 14, 2013.

(51) Int. Cl.
*C12P 13/00* (2006.01)
*C07C 227/04* (2006.01)

(52) U.S. Cl.
CPC .......... *C12P 13/001* (2013.01); *C07C 227/04* (2013.01)

(58) Field of Classification Search
CPC ............................. C12P 13/001; C07C 227/04
See application file for complete search history.

(56) References Cited

U.S. PATENT DOCUMENTS

| | | | |
|---|---|---|---|
| 3,702,255 A | 11/1972 | Finley et al. | |
| 3,766,261 A | 10/1973 | Finley | |
| 5,708,030 A | 1/1998 | Schwarcz et al. | |
| 5,789,434 A * | 8/1998 | Kluender ........... | A61K 31/4035 514/414 |

FOREIGN PATENT DOCUMENTS

| | | |
|---|---|---|
| WO | 95/04714 A1 | 2/1995 |
| WO | 2014/152752 A1 | 9/2014 |

OTHER PUBLICATIONS

Ross et al. Tetrahedron (1997) 53 (46), 15761-15770.*
Extended European Search Report in corresponding EP Application No. 14770640, dated Oct. 14, 2016.
Chenault et al., "Kinectic Resolution of Unnatural and Rarely Occurring Amino Acids: Enantioselective Hydrolysis of N-Acyl Amino Acids Catalyzed by Acylase I", J. Am. Chem. Soc., vol. 111, No. 16, 1989, pp. 6354-6364.
Andrews et al., A.J. J. Chem. Soc. Perkin Trans, 1995, pp. 1335-1340.
May et al., "Development of Dynamic Kinetic Resolution Processes for Biocatalytic Production of Natural and Nonnatural L-Amino Acids", Org. Pro. Res. Dev., 2002, pp. 452-457.
McCague et a., Crosby J. (Ed), John Wiley &Sons, 1997, pp. 195-200.
Sugasawa et al., "Aminohaloborane in Organic Synthesis. 1. Specific Ortho Substitution Reaction of Anilines", J. Org. Chem. 1977, pp. 4842-4852.
Sugasawa et al., "Aminohaloborane in Organic Synthesis. 2. Simple Synthesis of Indoles and 1-Acyl-3-indolinones Using Specific Ortho x-Chloroacetylation of Anilines", J. Org. Chem. 1979, 44, pp. 578-586.
International Preliminary Report on Patentability in International Application No. PCT/US2014/027694, dated Sep. 24, 2015.
International Search Report in International Application No. PCT/US2014/027694, dated Jul. 18, 2014.
Stone, T.W.; Pharmacol. Rev. 1993, 45, pp. 309-379.
Camacho et al.; J. Med. Chem. 2002, 45, pp. 263-274.
Varasi et al.; Eur. J. Med. Chem. 1996, 31, pp. 11-21.
Salituro et al.; J. Med. Chem. 1994, 37, pp. 334-336.
Imamoto, T., "Asymmetric Hydrogenation," Chapter 1; INTECH; http://dx.doi.org/10.5772/48584; 2012; pp. 1-30; section 31; p. 5.
Greene et al., "Protective Groups in Organic Synthesis," 3rd Edition; John Wiley and Sons; 1999; formamide cleavage; acetamide cleavage; pp. 551-553.
Fessenden et al., Organic Chemistry; 4th Edition; Wadsworth Inc.; 1990; pp. 651-652.
Kleijn et al., "A Concise preparation of the non-proteinogenic amino acid L-kynurenine; Tetrahedron Letters," vol. 53; 2012; pp. 6430-6432; second column, last paragraph p. 6430; scheme 2, p. 6431.
Jackson et al., "Carbonylative coupling of organozinc reagents in the presence and absence of aryl iodides: synthesis of unsymmetrical and symmetrical ketones," J. Chem. Soc., Perkin Trans. 1, 1997, pp. 865-870.
Wenqing et al., "Amino Acid Anhydride Hydrochlorides as Acylating Agents in Friedel-Crafts Reaction: A Practical Synthesis of I-Homophenylalanine," Abstract, Synthesis 2001(7).
Yan et a., "Synthesis of novel chiral oxazoline ligands and application in the highly enantioselective diethylzinc addition to N-diphenylphosphinoylimines," ScienceDirect, Tetrahedron, Asymmetry 18 (2007), 2643-2648.
Yato et al., "Reduction of Aromatic Ketones into Methylenes Using Triethylsilane and Titanium Tetrachloroide Synthesis of 2-Aminobutanoic Acids," Communication, Regular Issue, vol. 41, No. 1, 1995, pp. 17-20.

(Continued)

*Primary Examiner* — Alexander Kim
(74) *Attorney, Agent, or Firm* — J.A. Lindeman & Co., PLLC

(57) ABSTRACT

Provided are methods for synthesizing compounds, including chiral kynurenine compounds. The methods are suitable for large-scale manufacture and produce the chiral kynurenines compounds in high chemical purity and high chiral purity.

16 Claims, No Drawings

(56) References Cited

OTHER PUBLICATIONS

Cinelli et al., "The structure-activity relationships of A-ring-substituted aromathecin topoisomerase I inhibitors strongly support a camptothecin-like binding mode," Bioorganic and Medicinal Chemistry 18 (2010), pp. 5535-5552.

Melillo et al., "Practical Enantioselective Synthesis of a Homotyrosine Derivative and (R,R)-4-Propyl-9-hydroxynaphthoxazine, a Potent Dopamine Agonist," J. Org. Chem., 1987, 52, pp. 5143-5150.

Miao et al., "New homocamptothecins: Synthesis, antitumor activity, and molecular modeling," Bioorganic and Medicinal Chemistry 16 (2008), pp. 1493-1510.

Coppi et al., Chirality in Industry II, "Developments in the Commercial Manufacture and Applications of Optically Active Compounds", Edited by A.N. Collins; 1997, pp. 353-362.

* cited by examiner

METHODS FOR THE SYNTHESIS OF CHIRAL KYNURENINE COMPOUNDS

CROSS REFERENCE TO RELATED APPLICATION

This application claims priority to U.S. Provisional Patent Application No. 61/785,807, filed Mar. 14, 2013, the disclosure of which is hereby incorporated by reference in its entirety.

TECHNICAL FIELD

The present inventions relate to methods for synthesizing compounds, including chiral kynurenine compounds and related compounds.

BACKGROUND

Kynurenic acid is a metabolically related brain constituent with anticonvulsant and neuroprotective properties (Stone, T. W.; *Pharmacol. Rev.* 1993, 45, 309-379). The biological activities of various derivatives of the kynurenic acid and their kynurenine precursors have been studied (Camacho, E. et al. *J. Med. Chem.* 2002, 45, 263-274; Varasi, M. et al. *Eur. J. Med. Chem.* 1996, 31, 11-21; Salituro, F. G. et al. *J. Med. Chem.* 1994, 37, 334-336). Kynurenine compounds are converted to kynurenic acids in vivo.

An enantioselective synthesis described by Salituro et al. was used for the synthesis of gram quantities of L-4-chlorokynurenine (Salituro, F. G. et al. *J. Med. Chem.* 1994, 37, 334-336). This synthesis was not practical for scale up on a larger manufacturing scale due to the use of reagents such as trimethyl tin chloride, sodium hydride and tert-butyllithium and the lack of availability of certain building blocks.

A racemic synthesis of 4-chlorokynurenine was reported in Varasai et al. *Eur. J. Med. Chem.* 1996, 31, 11-21. However, experiments for the separation of the enantiomers by crystallization of diasteromeric salts were not successful, nor was preparative HPLC substantially successful, due to low solubility.

There is a need for a convenient synthesis for chiral kynurenines and related compounds using commercially available reagents that does not require the use of toxic or highly reactive reagents or extensive purification techniques. There is a need for syntheses suitable for large-scale manufacture and that can produce chiral kynurenines and related compounds in high chemical purity and high chiral purity.

All publications, patents, and patent applications cited herein are hereby incorporated by reference in their entirety for all purposes.

SUMMARY

Provided are methods for the synthesis of compounds including chiral kynurenine compounds and related compounds. In a specific embodiment, methods are provided for the synthesis of L-4-chlorokynurenine. In certain embodiments, the syntheses advantageously use commercially available reagents and avoid the use of toxic or highly reactive reagents or extensive purification techniques. In certain embodiments, syntheses are provided that are suitable for large-scale manufacture and that can produce compounds including the chiral kynurenines compounds and related compounds in high chemical purity and high chiral purity.

In one embodiment, the present disclosure provides a method of preparing a compound of Formula I or a pharmaceutically acceptable salt, polymorph, hydrate, solvate, tautomer, or stereoisomer thereof:

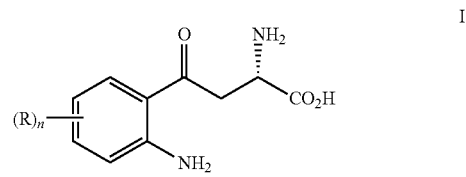

wherein each R is independently selected from the group consisting of hydrogen, halogen, alkyl, and substituted alkyl; and
wherein n=0-4;
the method comprising:
a) acylating an aniline compound of Formula II with chloroacetonitrile in the presence of aluminum trihalide and boron trihalide to afford an acylated aniline compound of Formula III:

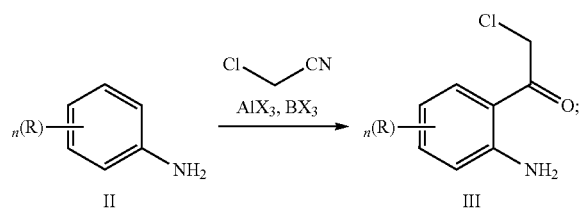

b) alkylating the acylated aniline compound of Formula III with acetamido diethyl malonate to afford a diethyl ester compound of Formula IV:

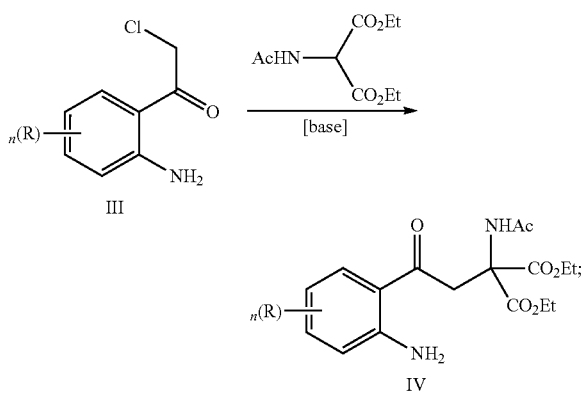

c) decarboxylating the diethyl ester compound of Formula IV to afford an acylated kynurenine compound of Formula V:

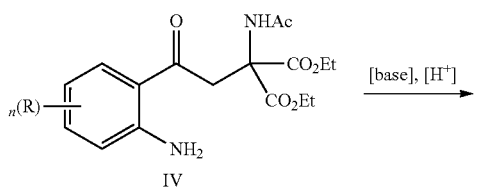

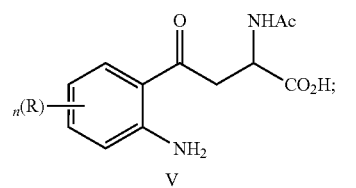

and d) resolving the acylated kynurenine compound of Formula V with an enzyme to afford the compound of Formula I:

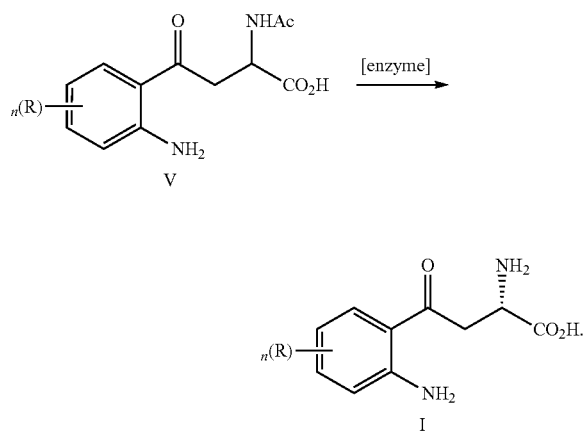

In some embodiments, the enzyme is acylase I from *Aspergillus melleus*. In other embodiments, at least 10 g of the compound of Formula I is produced. In other embodiments, at least 100 g of the compound of Formula I is produced. In other embodiments, at least 500 g of the compound of Formula I is produced. In other embodiments, the acylating step a) comprises adding the chloroacetonitrile to a toluene solution of the aniline compound II, the boron trihalide, and the aluminum trihalide at a first temperature of 0 to 10° C. followed by heating to a second temperature of 55 to 60° C. In other embodiments, the alkylating step b) is carried out in the presence of an alkali metal salt. In other embodiments, the alkali metal salt is sodium iodide.

In another embodiment, the present disclosure provides a method of preparing a compound of Formula Ia:

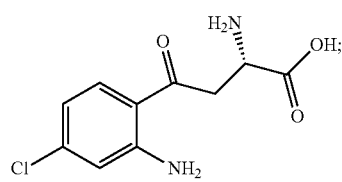

the method comprising:

a) acylating 3-chloroaniline (IIa) with chloroacetonitrile in the presence of aluminum trihalide and boron trihalide to afford 1-(2-amino-4-chloro-phenyl)-2-chloro-ethanone (IIIa):

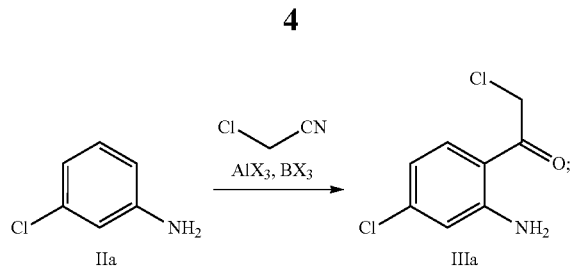

b) alkylating 1-(2-amino-4-chloro-phenyl)-2-chloro-ethanone (IIIa) with acetamido diethyl malonate to afford 2-acetylamino-2-[2-(2-amino-4-chloro-phenyl)-2-oxo-ethyl]-malonic acid diethyl ester (IVa):

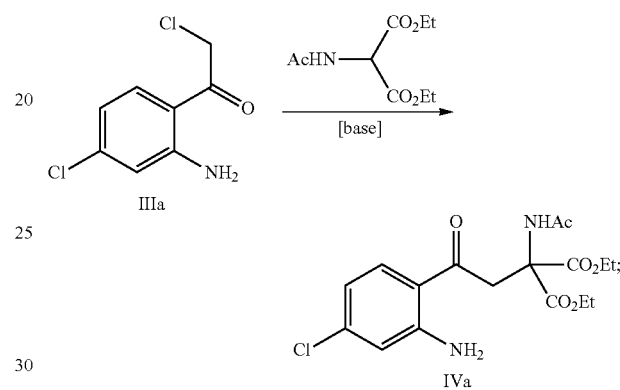

c) decarboxylating 2-acetylamino-2-[2-(2-amino-4-chloro-phenyl)-2-oxo-ethyl]-malonic acid diethyl ester (IVa) to afford 2-acetylamino-4-(2-amino-4-chloro-phenyl)-4-oxo-butyric acid (Va):

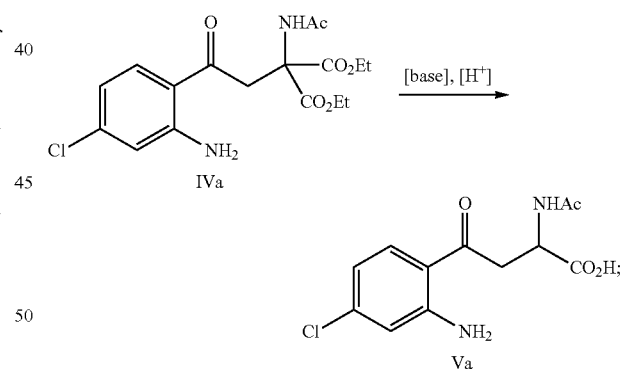

and d) resolving 2-acetylamino-4-(2-amino-4-chloro-phenyl)-4-oxo-butyric acid (Va) with an enzyme to the compound of Formula Ia:

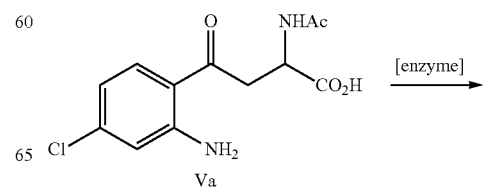

-continued

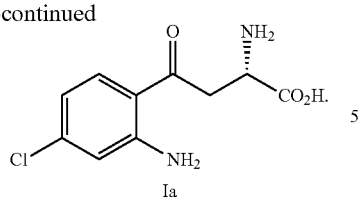

In some embodiments, the enzyme is acylase I from *Aspergillus melleus*. In other embodiments, at least 10 g of the compound of Formula Ia is produced. In other embodiments, at least 100 g of the compound of Formula Ia is produced. In other embodiments, at least 500 g of the compound of Formula Ia is produced. In other embodiments, the acylating step comprises adding the chloroacetonitrile to a toluene solution of the 3-chloroaniline, the boron trihalide, and the aluminum trihalide at a first temperature of 0 to 10° C. followed by heating to a second temperature of 55 to 60° C. In other embodiments, the alkylating step is carried out in the presence of an alkali metal salt. In other embodiments, the alkali metal salt is sodium iodide.

DETAILED DESCRIPTION

Provided are methods of preparing compounds, including chiral kynurenine compounds and related compounds.

Definitions

The term "alkyl" includes saturated aliphatic groups including straight-chain, branched-chain, cyclic groups, and combinations thereof. Examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, neopentyl, cyclopropyl, cyclobutyl, cyclopentyl, cyclohexyl, and adamantyl. Cycloalkyl groups can consist of one ring, including, but not limited to, groups such as cycloheptyl, or multiple fused rings, including, but not limited to, groups such as adamantyl or norbornyl.

"Substituted alkyl" includes alkyl groups substituted with one or more substituents including, but not limited to, groups such as halogen (fluoro, chloro, bromo, and iodo), alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkyl groups include, but are not limited to, —CF$_3$, —CF$_2$CF$_3$, and other perfluoro and perhalo groups; —CH$_2$—OH; —CH$_2$CH$_2$CH(NH$_2$)CH$_3$, etc.

The term "halogen," "halide," or "halo" as used herein includes the Group VIIa elements (Group 17 elements in the 1990 International Union of Pure and Applied Chemistry (IUPAC) Periodic Table, IUPAC Nomenclature of Inorganic Chemistry, Recommendations 1990) and includes fluoro, chloro, bromo, and iodo substituents.

Compounds

A variety of compounds, including chiral kynurenine compounds and related compounds, may be synthesized using the methods disclosed herein. In some embodiments, a compound of Formula I may be synthesized, or a pharmaceutically acceptable salt, polymorph, hydrate, solvate, tautomer, or stereoisomer thereof:

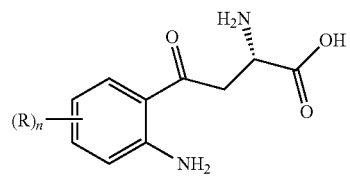

wherein each R is independently selected from the group consisting of hydrogen, halogen, alkyl, and substituted alkyl; and wherein n=0 to 4.

Where a chiral center is shown, any stereoisomer is within the scope of the invention. Where an (S) isomer is disclosed, the corresponding (R) isomer is within the scope of the invention. Where an (L) isomer is disclosed, the corresponding (D) isomer is within the scope of the invention. Where an (R) isomer is disclosed, the corresponding (S) isomer is within the scope of the invention. Where a (D) isomer is disclosed, the corresponding (L) isomer is with in the scope of the invention.

In a particular embodiment the compound is L-4-chlorokynurenine (Ia), which also is referred to by the chemical name (S)-2-amino-4-(2-amino-4-chlorophenyl)-4-oxobutanoic acid:

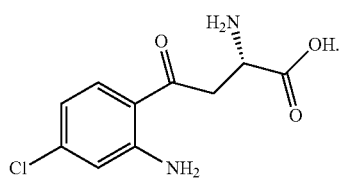

Where a compound is described herein, all stereoisomers thereof are also contemplated, including diastereomers and enantiomers, as well as mixtures of stereoisomers, including, but not limited to, racemic mixtures.

Some compounds of the present invention may exhibit polymorphism. The scope of the present invention includes all polymorphic forms of the compounds according to the invention.

Methods of Preparation

Methods of preparing a compound, for example of Formula I, or a pharmaceutically acceptable salt, polymorph, hydrate, solvate, tautomer, or stereoisomer thereof are provided:

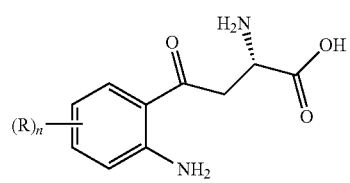

wherein each R is independently selected from the group consisting of hydrogen, halogen, alkyl, and substituted alkyl; and wherein n=0 to 4.

Also provided is a method of preparing a compound, for example of Formula I, or a pharmaceutically acceptable salt, polymorph, hydrate, solvate, tautomer, or stereoisomer thereof:

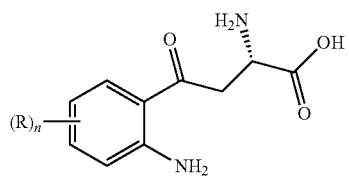

I wherein each R is independently selected from the group consisting of hydrogen, halogen, alkyl, and substituted alkyl; and wherein n=0-4;

the method comprising:

a) acylating an aniline compound of Formula II with chloroacetonitrile in the presence of aluminum trihalide and boron trihalide to afford an acylated aniline compound of Formula III:

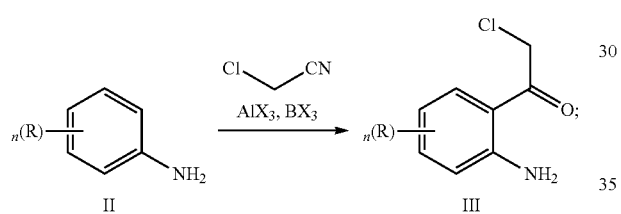

b) alkylating the acylated aniline compound of Formula III with acetamido diethyl malonate to afford a diethyl ester compound of Formula IV:

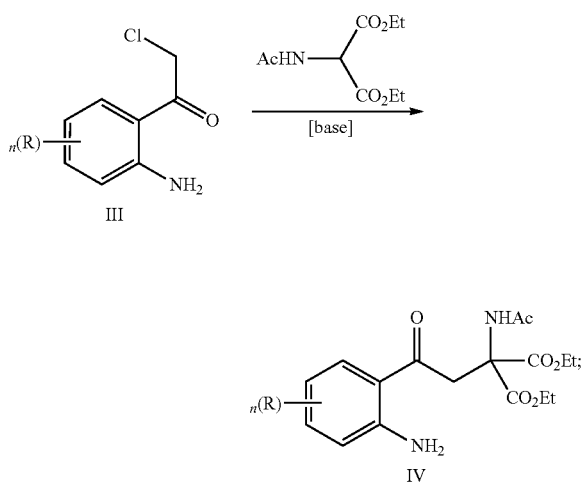

c) decarboxylating the diethyl ester compound of Formula IV to afford an acylated kynurenine compound of Formula V:

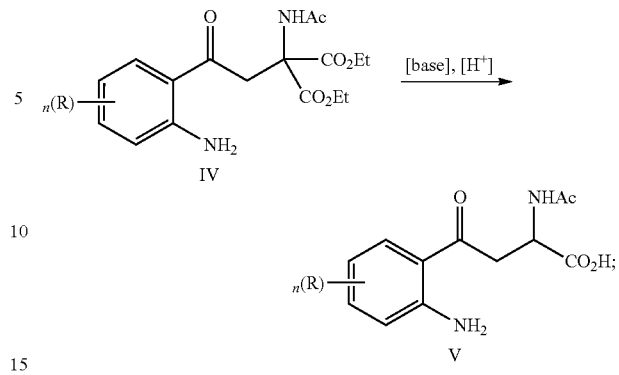

and d) resolving the acylated kynurenine compound of Formula V with an enzyme to afford the compound of Formula I:

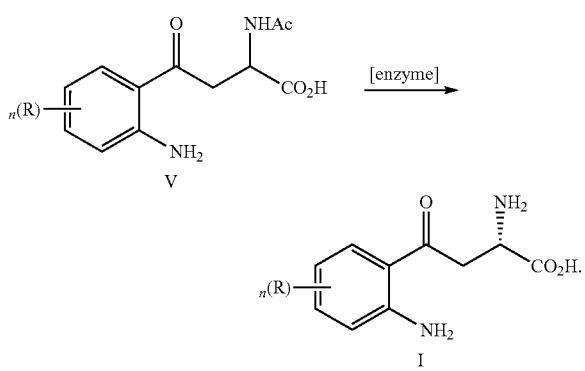

The R enantiomers of the compounds of Formulas I are also contemplated.

In one exemplary embodiment, the enzyme is acylase I from *Aspergillus melleus*. However, other acylase enzymes having similar functional, enzymatic activity would be known to persons skilled in the art.

In another embodiment, at least 10 g of the compound of Formula I is produced using the disclosed methods. In another embodiment, at least 100 g of the compound of Formula I is produced using the disclosed methods. In a particular embodiment, at least 500 g of the compound of Formula I is produced using the disclosed methods. Alternatively or additionally, the overall yield is at least 50% or more.

In another embodiment, the acylating step is carried out by adding chloroacetonitrile to a solution of aniline (II), boron trihalide, and aluminum trihalide in toluene at a temperature of about 0 to 10° C. followed by heating the reaction mixture to a temperature of about 55 to 60° C.

In another embodiment, the alkylating step is carried out in the presence of an alkali metal salt. Examples of such salts are the chloride, bromide, and iodide salts of sodium or potassium. In a preferred embodiment, the alkali metal salt is sodium iodide.

In another embodiment, provided is a method of preparing a compound of Formula Ia or a pharmaceutically acceptable salt, polymorph, hydrate, solvate, tautomer, or stereoisomer thereof:

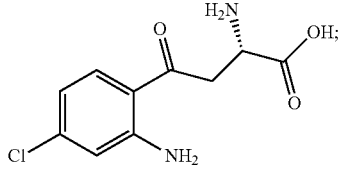

the method comprising:

a) acylating 3-chloroaniline (IIa) with chloroacetonitrile in the presence of aluminum trihalide and boron trihalide to afford 1-(2-amino-4-chloro-phenyl)-2-chloro-ethanone (IIIa):

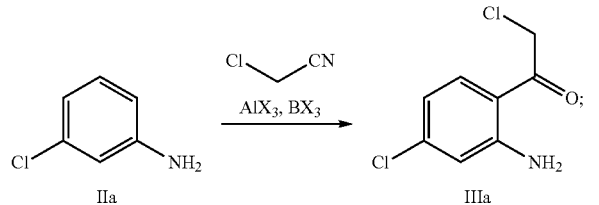

b) alkylating 1-(2-amino-4-chloro-phenyl)-2-chloro-ethanone (IIIa) with acetamido diethyl malonate to afford 2-acetylamino-2-[2-(2-amino-4-chloro-phenyl)-2-oxo-ethyl]-malonic acid diethyl ester (IVa):

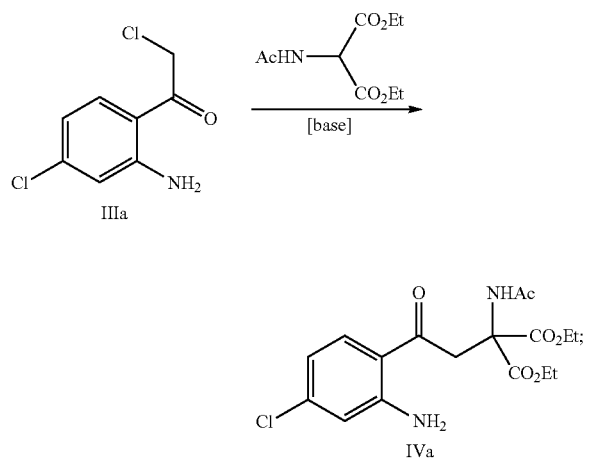

c) decarboxylating 2-acetylamino-2-[2-(2-amino-4-chloro-phenyl)-2-oxo-ethyl]-malonic acid diethyl ester (IVa) to afford 2-acetylamino-4-(2-amino-4-chloro-phenyl)-4-oxo-butyric acid (Va):

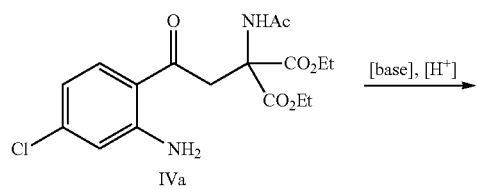

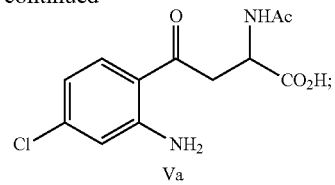

and d) resolving 2-acetylamino-4-(2-amino-4-chloro-phenyl)-4-oxo-butyric acid (Va) with an enzyme to afford the compound of Formula Ia:

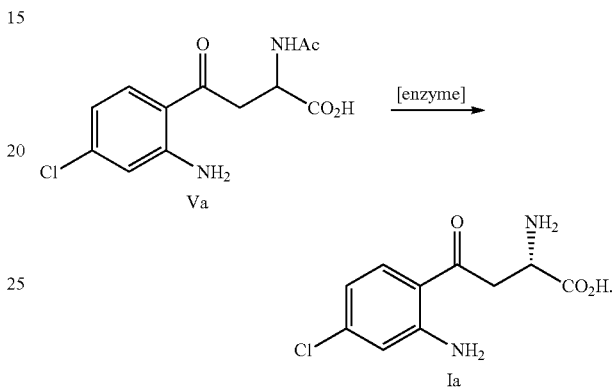

The R enantiomers of the compounds of Formulas Ia are also contemplated.

In one exemplary embodiment, the enzyme is acylase I from *Aspergillus melleus*. However, other acylase enzymes having similar functional, enzymatic activity would be known to persons skilled in the art.

In another embodiment, at least 10 g of the compound of Formula Ia is produced using the disclosed methods. In another embodiment, at least 100 g of the compound of Formula Ia is produced using the disclosed methods. In a particular embodiment, at least 500 g of the compound of Formula Ia is produced using the disclosed methods. Alternatively or additionally, the overall yield is at least 50% or more.

In another embodiment, the acylating step is carried out by adding chloroacetonitrile to a solution of aniline (IIa), boron trihalide, and aluminum trihalide in toluene at a temperature of about 0 to 10° C. followed by heating the reaction mixture to a temperature of about 55 to 60° C.

In another embodiment, the alkylating step is carried out in the presence of an alkali metal salt. Examples of such salts are the chloride, bromide, and iodide salts of sodium or potassium. In a preferred embodiment, the alkali metal salt is sodium iodide.

In certain embodiments, the methods allow for the production of compositions comprising compound of Formulas I or Ia in high purity, or in high enantiomeric excess. In some embodiments, a the composition comprising the compound of Formulas I or Ia is provided in a range of about 95% to about 100% for both chemical purity and enantiomeric excess. In some embodiments, a the composition comprising the compound of Formulas I or Ia is provided with about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% purity. In other embodiments, compositions comprising the compound of Formulas I or Ia have a high enantiomeric purity of a desired enantiomer in about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and 100% enantiomeric excess (ee).

The invention will be further understood by the following non-limiting examples.

Materials and Methods

Reagents and solvents were used as received from commercial suppliers. HPLC analyses were performed using a TSP-SpectraSYSTEM HPLC in a Water Symmetry Shield RP18, 75×4.6 mm. Solvents, water/acetonitrile/0.1% TFA in water-acetonitrile (9:1); gradient, 80:10:10 to 0:90:10 in 12 min then 80:10:10; flow rate, 1 ml/min; wavelength, 230 nm. Enantiomeric excess was determined by TSP-SpectraSYSTEM HPLC on a Chirobiotic T, 250×4.6 mm. Solvents, water/ethanol 1:1; flow rate, 1 ml/min; wavelength, 230 nm; $t_R$ 6.13 for L-isomer and 15.60 min for D-isomer. HPLC analyses are reported in area %.

Example 1

Preparation of 1-(2-Amino-4-chloro-phenyl)-2-chloro-ethanone (IIIa)

At a jacket temperature of 0° C., 1 M $BCl_3$ in dichloromethane (45 L, 45 mol, 1.1 equiv) was transferred into the reactor and toluene (13 L) was added. At −5 to 3° C. a solution of 3-chloroaniline (IIa, 4.5 L, 42 mol) in toluene (39 L) was added over 38 min followed after 31 min by aluminum trichloride (5.8 kg, 43 mol, 1.0 equiv). After 3 min, a solution of chloroacetonitrile (3.4 L, 54 mol, 1.3 equiv) in toluene (3.4 L) was added at −4 to 6° C. during 10 min. Heating to 65° C. at a maximal jacket temperature of 100° C. took 47 min, the mixture was stirred at 65° C. overnight. The reaction mixture was added to 1N aqueous HCl (81 L) over 41 min at 43° C. and stirred for 30 min at 48° C. After cooling to 20° C., the phases were separated and the aqueous phase was extracted twice with dichloromethane (2×40 L). The combined organic phases were washed with water (20.5 L). Dichloromethane (75 L) was removed by distillation under reduced pressure (jacket temperature 45° C.) and heptane (55 L) was added to the solution at 40° C. Cooling to 5° C., filtration, and washing with heptane (15 L) led to isolation of 1-(2-amino-4-chloro-phenyl)-2-chloro-ethanone (IIIa, 2.5 kg, 12 mol, 29% yield, 99.2% a/a HPLC).

Example 2

Preparation of 2-Acetylamino-2-[2-(2-amino-4-chloro-phenyl)-2-oxo-ethyl]-malonic acid diethyl ester (IVa)

To a solution of acetamido diethyl malonate (5.87 kg, 27.0 mol, 1.01 equiv) in ethanol (31.5 L) was added 21% sodium ethoxide in ethanol (12.1 L, 32.4 mol, 1.21 equiv) at 22° C. A mixture of 1-(2-amino-4-chloro-phenyl)-2-chloro-ethanone (IIIa, 5.44 kg, 26.7 mol), sodium iodide (0.60 kg, 4.0 mol, 0.15 equiv), ethanol (17 L), and tetrahydrofuran (THF, 17 L) was dosed into the reactor at 40° C. and stirring was continued for 2 h at 45° C. Water (36 L) was added after evaporation of the reaction mixture to 45% of the original volume and the aqueous phase was extracted twice with dichloromethane (34.5 L, 20 L). The combined organic phases were washed with water (14 L). After removal of 25% of the original volume by distillation under reduced pressure, isopropanol (32 L) was added and 50% thereof distilled off. At 60° C., heptane (11 L) was added. Cooling the mixture to 5° C., filtration and washing with isopropanol/heptane 1:1 (15 L) afforded 2-acetylamino-2-[2-(2-amino-4-chloro-phenyl)-2-oxo-ethyl]-malonic acid diethyl ester (IVa, 5.86 kg, 15.2 mol, 57% yield, 99.5% a/a HPLC).

Example 3

Preparation of 2-Acetylamino-4-(2-amino-4-chloro-phenyl)-4-oxo-butyric acid (Va)

A solution of 2-acetylamino-2-[2-(2-amino-4-chloro-phenyl)-2-oxo-ethyl]-malonic acid diethyl ester (IVa, 5.80 kg, 15.1 mol) in water (3.8 L), dioxane (55 L) and 30% NaOH (7.7 L, 76.8 mol, 5.09 equiv) was heated to reflux at a jacket temperature of 110° C. for 45 min. Acetic acid (12.0 L) was added at 65-70° C. and the suspension was heated to reflux while maintaining a jacket temperature of 110° C. for 1.5 h. Saturated aqueous NaCl (30 L) and ethyl acetate (54 L) were added at 20° C., the phases separated, and the aqueous phase was extracted with ethyl acetate/dioxane 1:1 (40 L). The combined organic phases were then washed with a saturated aqueous solution of NaCl (14.5 L). The organic phase was evaporated to dryness (the product crystallized prior to complete evaporation) and stripped with ethanol (15.5 L) to afford 2-acetylamino-4-(2-amino-4-chloro-phenyl)-4-oxo-butyric acid (Va, 3.65 kg, 12.8 mol, 85% yield, 92.7% a/a HPLC).

Example 4

Preparation of L-4-Chlorokynurenine (Ia)

A solution of 2-acetylamino-4-(2-amino-4-chloro-phenyl)-4-oxo-butyric acid (Va, 3.57 kg, 12.6 mol) in water (52 L) and 0.1 M cobalt(II) chloride solution (108 mL, 0.01 mol) was heated to 35° C. Addition of 5 M LiOH in water (2.55 L, 12.8 mol, 1.02 equiv) gave a solution (pH=8.5) to which Acylase I (0.79 kg) in water (3.0 L) was added (pH=7.3). The pH was adjusted to 8.6 by addition of 5 M LiOH in water (0.21 L) and stirred for 19 h. Ethyl acetate/THF 1:1 (15.5 L) was added at 20° C. and the mixture acidified with 32% aqueous HCl (2.1 L). The layers were separated and the aqueous phase was filtered via a Zetacarbon and inline filter. The organic phase was extracted twice with 0.1 N HCl (2×11 L). The filtrate was extracted twice with ethyl acetate/THF (2×13.5 L). The aqueous layer was also filtered via a Zetacarbon and inline filter. Butanol (8.0 L) was added and the volume reduced to 7 L by azeotropic distillation at reduced pressure. The pH was adjusted to 6.2 by addition of 5 M LiOH (3.7 L) and 32% aqueous HCl (0.5 L). Cooling to 5° C., filtration and washing with water (2×1.5 L) provided crude L-4-chlorokynurenine (Ia). Dissolution of L-4-chlorokynurenine (Ia) in water (4.0 L) and 5 M LiOH (1.4 L) at pH=11 to 12, filtration of the residue, washing with 0.1 M LiOH (2×0.33 L) and readjusting the pH to 6.2 by addition of 32% aqueous HCl (0.8 L) led to a suspension. Filtration and washing the filter cake with water (2×1.0 L) and ethanol (1.0 L) afforded L-4-chlorokynurenine (Ia, 605 g, 2.49 mol, 19.8% yield, 98.8% a/a HPLC).

We claim:

1. A method of preparing a compound of Formula I or a pharmaceutically acceptable salt, polymorph, hydrate, solvate, tautomer, or stereoisomer thereof:

13

I wherein each R is independently selected from the group consisting of hydrogen, halogen, alkyl, and substituted alkyl; and wherein n=0-4;

the method comprising:

a) acylating an aniline compound of Formula II with chloroacetonitrile in the presence of aluminum trihalide and boron trihalide to afford an acylated aniline compound of Formula III:

II → III b) alkylating the acylated aniline compound of Formula III with acetamido diethyl malonate to afford a diethyl ester compound of Formula IV:

III → IV c) decarboxylating the diethyl ester compound of Formula IV to afford an acylated kynurenine compound of Formula V:

IV →

14

V and d) resolving the acylated kynurenine compound of Form an acylase enzyme to afford the compound of Formula I:

V → I

2. The method of claim 1, wherein the enzyme is acylase I from *Aspergillus melleus*.

3. The method of claim 1, wherein at least 10 g of the compound of Formula I is produced.

4. The method of claim 3, wherein at least 100 g of the compound of Formula I is produced.

5. The method of claim 4, wherein at least 500 g of the compound of Formula I is produced.

6. The method of claim 1, wherein the acylating step a) comprises adding the chloroacetonitrile to a toluene solution of the aniline compound II, the boron trihalide, and the aluminum trihalide at a first temperature of 0 to 10° C. followed by heating to a second temperature of 55 to 60° C.

7. The method of claim 1, wherein the alkylating step b) is carried out in the presence of an alkali metal salt.

8. The method of claim 7, wherein the alkali metal salt is sodium iodide.

9. A method of preparing a compound of Formula Ia or a pharmaceutically acceptable salt, polymorph, hydrate, solvate, tautomer, or stereoisomer thereof:

Ia the method comprising:

a) acylating 3-chloroaniline (IIa) with chloroacetonitrile in the presence of aluminum trihalide and boron trihalide to afford 1-(2-amino-4-chloro-phenyl)-2-chloro-ethanone (IIIa):

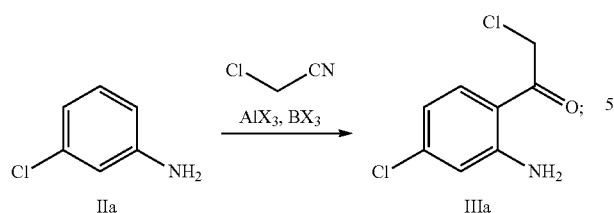

b) alkylating 1-(2-amino-4-chloro-phenyl)-2-chloro-ethanone (IIia) with acetamido diethyl malonate to afford 2-acetylamino-2-[2-(2-amino-4-chloro-phenyl)-2-oxoethyl]-malonic acid diethyl ester (IV a):

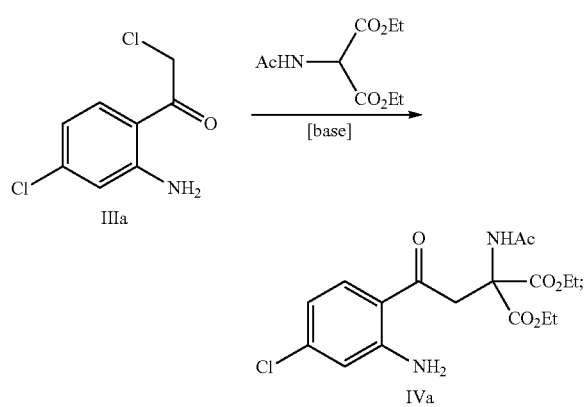

c) decarboxylating 2-acetylamino-2-[2-(2-amino-4-chlorophenyl)-2-oxo-ethyl]-malonic acid diethyl ester (IVa) to afford 2-acetylamino-4-(2-amino-4-chloro-phenyl)-4-butyric acid (Va):

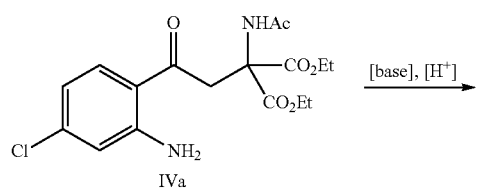

and d) resolving 2-acetylamino-4-(2-amino-4-chloro-phenyl)-4-oxo-butyric acid (Va) with an acylase enzyme to the compound of Formula Ia:

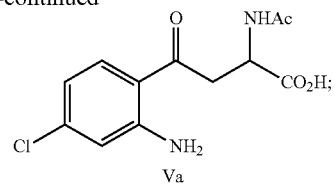

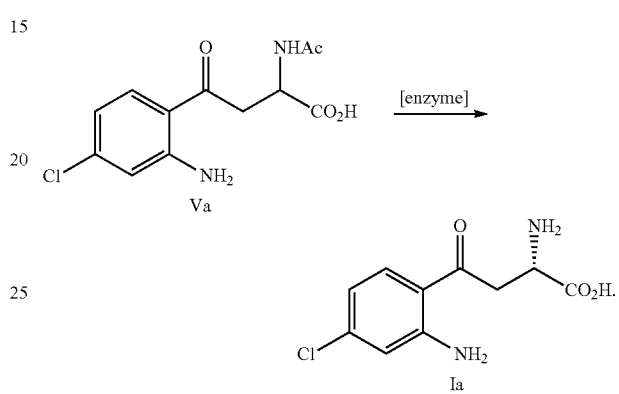

10. The method of claim 9, wherein the enzyme is acylase I from *Aspergillus melleus*.

11. The method of claim 9, wherein at least 10 g of the compound of Formula Ia is produced.

12. The method of claim 11, wherein at least 100 g of the compound of Formula Ia is produced.

13. The method of claim 12, wherein at least 500 g of the compound of Formula Ia is produced.

14. The method of claim 9, wherein the acylating step comprises adding the chloroacetonitrile to a toluene solution of the 3-chloroaniline, the boron trihalide, and the aluminum trihalide at a first temperature of 0 to 10° C. followed by heating to a second temperature of 55 to 60° C.

15. The method of claim 9, the alkylating step is carried out in the presence of an alkali metal salt.

16. The method of claim 15, wherein the alkali metal salt is sodium iodide.

* * * * *